United States Patent [19]

Heimreid

[11] 4,134,832

[45] Jan. 16, 1979

[54] METHOD AND DEVICE FOR TREATMENT OF BLOOD

[76] Inventor: Ken Heimreid, Brånanveien 44B, 3940 Heistad, Norway

[21] Appl. No.: 837,413

[22] Filed: Sep. 28, 1977

[30] Foreign Application Priority Data

Sep. 30, 1976 [NO] Norway ............................ 763337

[51] Int. Cl.² ...................... B01D 21/26; G01N 33/16
[52] U.S. Cl. .................................. 210/78; 23/230 B; 210/DIG. 23; 210/516; 233/26; 422/101
[58] Field of Search .............. 23/230 B, 259, 253 R; 73/64.1; 210/DIG. 23, 78, 516

[56] References Cited

U.S. PATENT DOCUMENTS

| | | | |
|---|---|---|---|
| 3,894,950 | 7/1975 | Ayres et al. | 210/DIG. 23 |
| 3,919,085 | 11/1975 | Ayres | 210/DIG. 23 |
| 3,920,557 | 11/1975 | Ayres | 210/DIG. 23 |
| 3,960,727 | 6/1976 | Hochstrasser | 210/DIG. 23 |
| 3,963,119 | 6/1976 | Lukacs et al. | 210/DIG. 23 |
| 3,972,812 | 8/1976 | Gresl, Jr. | 210/DIG. 23 |
| 4,021,352 | 5/1977 | Sarstedt | 210/DIG. 23 |
| 4,055,501 | 10/1977 | Cornell | 210/DIG. 23 |

*Primary Examiner*—R. E. Serwin
*Attorney, Agent, or Firm*—Cushman, Darby & Cushman

[57] ABSTRACT

Uncoagulated blood is separated into components by placing the blood in a glass test tube, placing a porous, elastic body in the upper layer of the blood, and centrifuging such that the porous body in friction contact with the inner surface of the test tube is pressed down through the blood so as to form above the body a layer of serum overlying a layer of red cells which overlies the body.

9 Claims, 7 Drawing Figures

Fig. 1
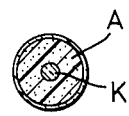
Fig. 2
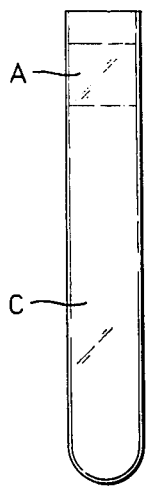
Fig. 3
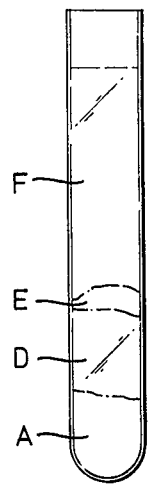
Fig 4
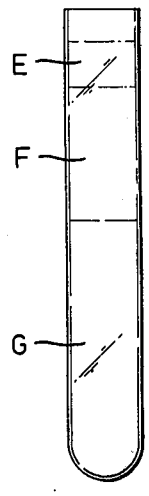
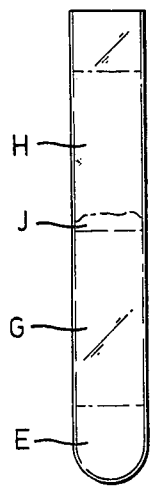
Fig. 5
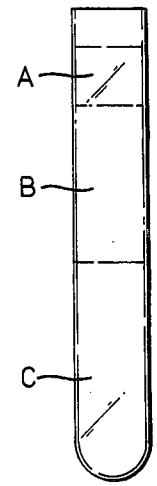
Fig. 6
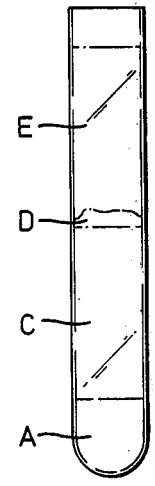
Fig. 7

METHOD AND DEVICE FOR TREATMENT OF BLOOD

The present invention relates to a method and a means for separating uncoagulated blood by centrifugation thereby facilitating the subsequent analysis of the blood.

In order to obtain a blood serum suitable for analysis or other further treatment, one has previously been forced to place the blood in a test tube for up to 30 minutes so that the blood will coagulate before it is centrifuged. In the first place, this coagulation time causes an undesirable delay in carrying out the required analysis, for example, when the blood is required in an emergency situation, and, secondly, the serum following centrifugation is not fibrin-free, and the red blood corpuscles are for the most surrounded by fibrin as the coagel. This in turn results in a not-insignificant decrease in volume of the total serum in the blood.

The applicant has now discovered that if a porous body is pressed down through uncoagulated blood during centrifugation, a rapid activation of the total fibrinogen in the blood occurs, the fibrinogen being converted into a fibrin concentrate. This also holds true for uncoagulated blood to which anticoagulants have been added, provided the porous body has been impregnated with a suitable defibrinizing substance. The formation of coagel in the blood is thus entirely or partially prevented, depending on how quickly fibrin activation begins following the withdrawal of the blood sample. If the activation process commences promptly upon withdrawal of blood, therefore, the total volume of serum in the blood will be released.

As mentioned above, it has previously been necessary to allow the blood to stand for a time before the required centrifugation could be carried out.

It is obvious that time is a crucial factor in this type of work, and the present invention makes it possible to reduce this time to the minimum time required before preparations for the analysis of freshly-drawn blood or blood which has been treated with anticoagulants can commence.

The invention thus relates to a method of separating the components of uncoagulated blood, e.g., freshly-drawn blood or heparin blood, the method being characterized by the steps of filling a test tube of glass or having a glass-like surface with blood, placing a porous, elastic body in the upper layer of the blood, optionally, subsequent to a short pre-centrifugation, and centrifuging the blood such that the porous body, in friction contact with the inner surfaces of the test tube, is pressed down through the blood.

The porous body preferably consists of plastic foam and is cylindrical in shape, its diameter being greater than the diameter of the test tube. Therefore, when the body is inserted into the test tube, it will be compressed and seal around the edges of the tube.

The method of the invention makes it possible to subject blood which has just been withdrawn from a patient to immediate examination. The method applies equally to blood to which heparin, for example, may have been added to prevent the blood from coagulating during its journey from the place where the blood was withdrawn to the laboratory where analysis is to be carried out.

The invention also relates to a means for carrying out the method outlined above, the means being characterized in that it consists of a test tube of glass or having a glass-like surface and a porous, elastic body in which one or more ballast bodies may optionally be embedded.

Without wishing to be bound by any particular theories, the inventor assumes that a rapid activation of the total fibrinogen in the blood occurs because the porous body, during the centrifugation process and owing to friction, affects the inner walls of the test tube. The test tube is preferably made of glass, which in its natural state appears to have an activating effect on the fibrinogen. Plastic test tubes whose inner wall surfaces have been treated to give them the properties of glass, will also effect a rapid activation of the fibrinogen during centrifugation with the porous body. Such tubes could be made as disposable tubes, to be discarded after one use. Using a glass bead as a ballast means in the porous body will also increase fibrinogen activation during the centrifugation process.

As stated above, the present invention makes it possible to subject blood to examination immediately.

With freshly-drawn blood, centrifugation and the use of the porous body can commence immediately; with heparin blood and citrate blood, however, it is preferable that a quick preliminary centrifugation be carried out first, because this blood has a tendency to separate easily, with the red blood corpuscles at the bottom of the tube and the blood plasma, comprised of the serum and fibrinogen, in the upper part of the tube. Upon subsequent centrifugation with the use of the porous body, then, the fibrin in the plasma will be activated and fall out as fibrin, leaving pure serum in the upper part of the tube.

In treating blood to which an anticoagulant has been added, centrifugation is carried out with a porous body which has been impregnated with a defibrinizing substance. For heparin blood, protamine sulfate is preferred.

The invention will be further explained with reference to the drawings.

FIG. 1 is a schematic cross section of a plastic foam body in which a glass bead is embedded, seen at right angles to the tube axis.

FIG. 2 is a schematic drawing of a test tube with uncoagulated whole blood and the plastic foam body of FIG. 1 prior to centrifugation.

FIG. 3 shows the test tube of FIG. 2 following centrifugation.

FIG. 4 illustrates a test tube of citrate blood prior to the second centrifugation, with the plastic foam body at the top of the tube.

FIG. 5 shows the condition of the blood and porous body of FIG. 4 following the second centrifugation.

FIG. 6 shows a tube of heparin blood prior to the second centrifugation, with the plastic foam body at the top of the tube.

FIG. 7 shows the condition of the blood and porous body of FIG. 6 following the second centrifugation.

The plastic foam body A on FIG. 1 is cylindrical in shape, and has a central glass bead K as a ballast body. The porous body can also be made of another suitable material and can contain more than one ballast body, which may be made of another material than glass.

The plastic foam body A is placed, as shown on FIG. 2, in coagulated, freshly-drawn whole blood C in a test tube which is put into a centrifuge (not shown). During centrifugation, the foam body will be pressed through the blood toward the bottom of the test tube, and the blood will separate into layers, from bottom to top, of fibrin-free red corpuscles D, a fibrin clump E and purified, fibrin-free serum F, as shown on FIG. 3.

Prior to the second centrifugation of citrate blood (FIG. 4), a plastic foam body E, which is impregnated with the defibrinizing substance calcium chloride, is put into the plasma F which, following the first centrifugation of the citrate blood, lies above the red corpuscles G. Following the second centrifugation, as shown on FIG. 5, the plastic foam body will be pressed through the plasma F on FIG. 4 and the red corpuscles G on FIG. 5 to the bottom of the test tube, while the fibrin has become separated as a concentrate, a clump J, on the surface of the red corpuscles G and between the corpuscles G and the serum H which has formed above the fibrin clump J. The plastic foam body E is at the bottom of the test tube.

Prior to the second centrifugation of heparin blood, as shown on FIG. 6, the plastic foam body A, which has been impregnated with protamine sulfate, is placed in the plasma B which, following the first centrifugation, lies above the red corpuscles C. Following the second centrifugation, as shown on FIG. 7, the plastic foam body will have been pressed down through the plasma E on FIG. 6 and the red corpuscles C on FIG. 7 to the bottom of the test tube, while the fibrin has been separated and forms a concentrate clump D on the surface of the red blood cells C and beneath the serum E which now has formed above the fibrin clump D. The plastic foam body A is at the bottom of the test tube.

Having described my invention, I claim:

1. A method of separating uncoagulated blood into components by centrifugation comprising: placing a sample of uncoagulated blood in a test tube of glass or having a glass-like inner surface; placing a porous, elastic body in the upper layer of the uncoagulated blood sample; and centrifuging the test tube and blood sample to cause the porous body, in frictional contact with the inner surface of the test tube to press through the blood sample so as to effect above the porous body a layer of serum overlying a layer of red blood corpuscles which overlies the porous body.

2. A method as in claim 1 wherein said uncoagulated blood is precentrifuged without the presence of a porous elastic body.

3. A method as in claim 1 wherein said porous body moves all the way to the bottom of the test tube during centrifugation.

4. A method as in claim 1 wherein centrifugation and movement of the porous body effect a clump of fibrin between said serum layer and corpuscle layer.

5. A method as in claim 2 wherein the blood is heparin blood and wherein the proous elastic body is impregnated with a defibrinizing substance.

6. A method as in claim 5 wherein said defibrinizing substance is protamine sulfate.

7. Apparatus for separating uncoagulated blood into components during centrifuging comprising a test tube of glass or having a glass-like surface, and a porous elastic body insertable into said test tube so as to be in frictional contact with the inside thereof, said body having embedded therein at least one ballast body and being movable through the uncoagulated blood during centrifugation so as to come to rest below a red-cell layer which underlies a serum layer.

8. Apparatus as in claim 5 wherein said porous elastic body is made of plastic foam.

9. Apparatus as in claim 6 wherein said ballast body is a glass bead.

* * * * *